(12) United States Patent
Thomas et al.

(10) Patent No.: US 12,403,085 B2
(45) Date of Patent: Sep. 2, 2025

(54) HAIR COLORING WITH COCONUT OIL

(71) Applicant: L'OREAL, Paris (FR)

(72) Inventors: Jeeba Thomas, Morris Plains, NJ (US);
Amer Alkahwaji, Hoboken, NJ (US);
Wonhee Park, Teaneck, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/815,268

(22) Filed: Jul. 27, 2022

(65) Prior Publication Data

US 2024/0041751 A1 Feb. 8, 2024

(51) Int. Cl.
| | |
|---|---|
| *A61K 8/92* | (2006.01) |
| *A61K 8/22* | (2006.01) |
| *A61K 8/41* | (2006.01) |
| *A61K 8/49* | (2006.01) |
| *A61K 8/73* | (2006.01) |
| *A61Q 5/10* | (2006.01) |

(52) U.S. Cl.
CPC ............... *A61K 8/92* (2013.01); *A61K 8/22* (2013.01); *A61K 8/41* (2013.01); *A61K 8/49* (2013.01); *A61K 8/4973* (2013.01); *A61K 8/737* (2013.01); *A61Q 5/10* (2013.01); *A61K 2800/43* (2013.01); *A61K 2800/48* (2013.01); *A61K 2800/5426* (2013.01)

(58) Field of Classification Search
CPC ... A61K 8/92; A61K 8/22; A61K 8/41; A61K 8/49; A61K 8/4973; A61K 8/737; A61K 2800/43; A61K 2800/48; A61K 2800/5426; A61K 2800/5422; A61K 8/31; A61K 8/463; A61K 8/604; A61K 8/86; A61K 8/922; A61Q 5/10
See application file for complete search history.

(56) References Cited

U.S. PATENT DOCUMENTS

| | | | |
|---|---|---|---|
| 4,228,151 A | 10/1980 | Lang et al. | |
| 4,293,542 A | 10/1981 | Lang et al. | |
| 5,661,118 A | 8/1997 | Cauwet et al. | |
| 5,948,395 A | 9/1999 | Le Bras-Roulier et al. | |
| 6,132,742 A | 10/2000 | Le Bras et al. | |
| 7,550,015 B2 | 6/2009 | Legrand | |
| 7,699,897 B2 | 4/2010 | Nguyen et al. | |
| 7,811,552 B2 | 10/2010 | Maubru et al. | |
| 7,927,383 B2 | 4/2011 | Hercouet et al. | |
| 8,636,813 B2 | 1/2014 | Uellner et al. | |
| 9,789,034 B2 | 10/2017 | Rapold et al. | |
| 10,137,063 B2 | 11/2018 | Charrier et al. | |
| 10,154,954 B2 | 12/2018 | Arditty et al. | |
| 10,201,483 B2 | 2/2019 | Charrier et al. | |
| 10,226,411 B2 | 3/2019 | Charrier et al. | |
| 10,772,818 B2 | 9/2020 | DeGeorge et al. | |
| 11,090,256 B2 | 8/2021 | Ceballos et al. | |
| 2009/0028958 A1 | 1/2009 | Blin et al. | |
| 2009/0070945 A1 | 3/2009 | Nguyen et al. | |
| 2009/0123403 A1 | 5/2009 | Barba et al. | |
| 2013/0149274 A1 | 6/2013 | Nguyen et al. | |
| 2015/0110884 A1 | 4/2015 | Arditty et al. | |
| 2019/0117549 A1* | 4/2019 | Degeorge | A61K 8/678 |
| 2019/0201309 A1 | 7/2019 | Machover et al. | |
| 2021/0137821 A1 | 5/2021 | Crew | |
| 2022/0175626 A1 | 6/2022 | Qi et al. | |

FOREIGN PATENT DOCUMENTS

WO 2013083701 A1 6/2013

OTHER PUBLICATIONS

Preliminary Search Report and Written Opinion issued on Mar. 30, 2023 for corresponding French Application No. FR2209234.

* cited by examiner

*Primary Examiner* — Benjamin J Packard
*Assistant Examiner* — Lucy M Tien
(74) *Attorney, Agent, or Firm* — POLSINELLI PC

(57) ABSTRACT

The instant disclosure relates to hair coloring base compositions containing coconut oil, ready-to-use hair coloring compositions containing coconut oil, and methods for coloring hair. The hair coloring base composition includes: (a) coconut oil; (b) one or more oils other than coconut oil; (c) one or more alkalizing agents; (d) one or more oxidative dye precursors and/or couplers; (e) one or more surfactants; (f) one or more thickening agents; and (g) water. The hair coloring base compositions, the ready-to-use hair coloring compositions, and the methods provide vibrant and durable color to the hair while imparting moisturizing, styling, and anti-frizz properties to the hair; and are particularly useful for curly and very curly hair types.

28 Claims, No Drawings

HAIR COLORING WITH COCONUT OIL

FIELD OF THE DISCLOSURE

The present disclosure relates to hair coloring base compositions and ready-to-use hair coloring compositions comprising coconut oil. Methods for making the compositions and methods for coloring hair, especially curly and very curly hair, are also disclosed.

BACKGROUND

Consumers enjoy cosmetic products that enhance the appearance of keratinous substrates such as hair, e.g., by changing the color, style, and/or shape of the hair, and/or by imparting various properties to hair, such as shine and conditioning. Many of the known products and processes for enhancing the appearance of the hair involve chemical treatments.

The process of changing the color of hair, for example, can involve depositing an artificial color onto the hair which provides a different shade or color to the hair, these processes generally require oxidizing agent. The color change is typically evaluated by the variation in tone before and after the hair is colored. This variation corresponds to the degree or level of lightening or color deposit. The notion of "tone" is based on the classification of the natural shades, one tone separating each shade from the shade immediately following or preceding it, which is well known to hairstyling professionals. The tone levels range from 1 (black) to 10 (light blond), one unit corresponding to one tone; thus, the higher the number, the lighter the shade or the greater the degree of lift and vice versa.

In general, hair coloring compositions have an alkalinity such that these compositions have a pH value of above 7, typically being at pH 9 and above, and may rely on the presence of an alkalizing agent such as ammonia or an ammonia gas generating compound and/or an amine or ammonium-based compound in amounts sufficient to ensure the compositions are alkaline. The alkalizing agent causes the hair shaft to swell, thus allowing the small oxidative dye molecules to penetrate the cuticle and cortex before an oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While coloring compositions can effectively alter the color of hair, and relaxing, straightening, perming, and waving compositions can effectively alter the shape of the hair, these chemical treatments can damage the hair fibers and/or irritate the scalp. The damaged hair become dry, brittle, and tends to become frizzy. Thus, in order to reduce or avoid the drawbacks mentioned above, as well as to improve the cosmetic performance of the compositions, the use of new and additional components and novel combinations of ingredients are continuously sought. In particular, there is a need for effective and nourishing products for the treatment of curly hair and very curly hair, which provide unique challenges.

The choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It is therefore desirable to provide the consumer with compositions and methods that can color the hair in an efficient manner, while providing other cosmetic advantages such as shine, conditioning, fiber strength, and/or a healthy appearance to the hair, especially curly and very curly hair.

SUMMARY OF THE DISCLOSURE

There are various types of hair coloring compositions for temporarily, semi-permanently, and permanently coloring hair. Most types of hair coloring composition for permanently coloring hair are oxidative hair coloring compositions that use two parts. The first part is a hair coloring base composition that contains oxidative dye precursors (sometimes called "oxidative dyes") and couplers, which interact with the oxidative dye precursors. The second part is a developer composition containing an oxidizing agent like hydrogen peroxide. The two parts are mixed immediately prior to use forming a ready-to-use hair coloring composition to activate the composition for coloring the hair. Thus, ready-to-use hair coloring compositions can be called "active hair coloring compositions." The oxidative dye precursors and oxidizing agents from the active hair coloring compositions diffuse into the hair shaft, where color formation takes place through a cascade of chemical reactions. The oxidative dye precursors are oxidized by the oxidizing agents and form reactive intermediates. Couplers, which are relatively stable to oxidizing agents, react with the intermediates resulting in vibrant coloring molecules.

The hair coloring base compositions of the instant case include coconut oil, which provides a variety of beneficial cosmetic properties. The hair coloring base composition is combined with a developer composition to derive a ready-to-use hair coloring composition for coloring hair. The compositions are effective, durable (long-lasting) and provide styling benefits to the hair (e.g., hydration/moisturization, body, style definition including curl definition, anti-frizz properties, etc.). They are useful for coloring all types of hair including all types of hair of the head, eye lashes, eyebrows, and body but were surprisingly found to be particularly effective for addressing the needs of individuals with curly and very curly hair.

The hair coloring base compositions include:
(a) coconut oil;
(b) one or more oils other than coconut oil;
(c) one or more alkalizing agents;
(d) one or more oxidative dye precursors;
(e) one or more surfactants;
(f) one or more thickening agents; and
(g) water.

In addition to coconut oil, the hair coloring base composition include one or more additional oils other than coconut oil. The one or more additional oils are compatible with the coconut oil and are helpful for conditioning the hair. Nonlimiting examples of additional oils other than coconut oil include ester oils, silicone oils, fluoro oils, vegetable oils, animal oils, hydrocarbon-based oils, and a combination thereof. In various embodiments, at least one of the one or more oils is selected from halogenated or non-halogenated linear or branched hydrocarbons, of mineral or synthetic origin, containing less than 16 carbon atoms, for instance hexane, cyclohexane, undecane, dodecane, isododecane, tridecane or perfluorohexane, or more than 16 carbon atoms, such as liquid petroleum jelly. In a preferred embodiment, at least one of the one or more additional oils is mineral oil (paraffinum liquidum).

Alkalizing agents have multiple roles in the coloring process in addition to providing alkalinity to influence pH. Alkalizing agents help cause the hair shaft to swell, allowing the small oxidative dye precursor molecules to penetrate the cuticle and cortex more easily. Also, the alkalizing agents can activate one or more oxidizing agents of the developer composition and contribute to the oxidation condensation process.

Non-limiting examples of alkalizing agents include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof.

Nonlimiting examples of organic alkalizing agents include monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. Nonlimiting examples of mineral alkalizing agents include ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof.

In various embodiments, the hair coloring base composition is free or essentially free from mineral alkalizing agents. In another embodiment, the hair coloring base composition is free or essentially free from ammonia and/or ammonium ions, and/or ammonium hydroxide.

Nonlimiting examples of oxidation dye precursors (also referred to as "oxidation bases" include aromatic diamines, polyhydric phenols, amino phenols, and derivatives of these compounds, such as, for example, N-substituted derivatives of the amines, and ethers of the phenols, ortho- or para-aminophenols, ortho- or para-phenylenediamines, double bases, heterocyclic bases, and the acid addition salts thereof.

Nonlimiting examples of couplers include meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

The surfactants can be nonionic, anionic cationic, amphoteric (zwitterionic), cationic, or combinations thereof.

Nonlimiting examples of nonionic surfactants include alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30.

In various embodiments, the one or more nonionic surfactants are selected from non-silicone nonionic surfactants. Nonlimiting examples include straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof.

In various embodiments, the hair coloring base compositions include one or more nonionic surfactants. In further embodiments, the hair coloring base compositions include one or more nonionic surfactants and one of more anionic surfactants, preferably an alkoxylated nonionic surfactant, for example, a PEG-40 hydrogenated castor oil (nonionic surfactant) and an alkyl sulfate or alkyl ether sulfate such as sodium lauryl sulfate (anionic surfactant).

Nonlimiting examples of thickening agents include carboxylic acid polymers, crosslinked polyacrylate polymers, polyacrylamide polymers, polysaccharides, gums, and a combination thereof. In various embodiments, at least one of the one more thickening agents are selected from a guar gum and modified guar gums. Particularly preferred are nonionic guar gums and nonionic modified guar gums, for example, hydroxypropyl guar.

The hair coloring base compositions can optionally include one or more reducing agents. Reducing agents are chemical species that lose an electron to another chemical species in a redox chemical reaction. Nonlimiting examples of reducing agents include ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, thioglycerin, dehydroascorbic acid, a salt thereof, and a mixture thereof. In certain embodiments, the hair coloring base compositions include thioglycolic acid, thiolactic acid, thioglycerin, salts thereof, and mixtures thereof.

The hair coloring base compositions and the developer compositions are separately contained prior to mixing. Thus, both compositions can be provided in a single kit. Kits according include one or more hair coloring base compositions and one or more developer compositions, wherein the hair coloring base compositions and the developer compositions are separately contained. For example, the one or more hair coloring base compositions and the one or more developer compositions may be included in separate containers that are packaged together.

Methods for making a ready-to-use hair coloring compositions and methods for coloring hair with the compositions entail combining the hair coloring base composition with a developer composition to form a ready-to-use hair coloring composition. The ready-to-use hair coloring composition is then applied to hair for a period of time (for processing), for example, for about 1 to about 60 minutes, about 1 to 45 minutes, about 1 to about 30 minutes, or about 1 to about 15 minutes. After the period of time, the hair coloring compositions may be rinsed or washed from the hair exposing the newly colored hair. The newly colored hair durably retains its changed color, suffers little or no undesirable chemical damage, and the underlying skin is not subjected to burning and stinging at times associated with various oxidative coloring methods. Additionally, the newly colored hair exhibits improved styling benefits, such as improved curl retention and definition, less frizz, and improved moisturization/hydration.

DETAILED DESCRIPTION

The hair coloring compositions and methods of the instant case provide quick and powerful color deposition to the hair that is long-lasting (durable). The hair coloring compositions are suitable for all types of hair but surprisingly, were found to address the unique needs of individuals with curly and very curly hair.

As noted previously, hair coloring compositions for permanently altering the color of hair typically rely on a combination of two parts, a hair coloring base composition, and a developer composition. The hair coloring base composition includes oxidative dye precursors, and the developer composition includes oxidizing agents, like hydrogen peroxide. The two parts are mixed to form a ready-to-use hair coloring composition.

Oxidative dye precursors are typically colorless or weakly colored compounds, which, when combined with oxidizing agents, transition to provide colored species via a process of oxidative condensation. The shades obtained with oxidative dye precursors may be varied by combining them with one or more couplers. Couplers include, for example, aromatic meta-diamines, meta-aminophenols, meta-diphenols, and certain heterocyclic compounds, such as indole compounds.

The oxidizing agents used in permanent hair coloring compositions may degrade the melanin of the hair. A common oxidizing agent used in hair coloring processes is hydrogen peroxide. Nonetheless, peroxygenated salts, such as persulfates, may be used, often in conjunction with hydrogen peroxide.

In general, hair coloring compositions are alkaline, having a high pH of about 9 and higher, and may generally require the presence of an alkalizing agent such as ammonia or an ammonia gas-generating compound and/or an amine or ammonium-based compound in amounts sufficient to achieve the desired alkalinity. The alkalizing agents help activate the oxidizing agents and cause the hair shaft to swell, thus allowing the small oxidative dye precursor molecules to penetrate the cuticle and cortex before the oxidation condensation process is completed. The resulting larger-sized colored complexes from the oxidative reaction are then trapped inside the hair fiber, permanently altering the color of the hair.

In various embodiments, the hair coloring base composition includes:
(a) about 0.8 to about 2 wt. % of coconut oil;
(b) about 50 to about 75 wt. % of one or more oils other than coconut oil, in particular one or more hydrocarbons, of mineral or synthetic origin, containing less than 16 carbon atoms, for instance hexane, cyclohexane, undecane, dodecane, isododecane, tridecane or perfluorohexane, or more than 16 carbon atoms, such as mineral oil or liquid petroleum jelly;
(c) about 1 to about 10 wt. % of one or more alkalizing agents, preferably selected from alkanolamines, for example, monoethanolamine;
(d) one or more oxidative dye precursors and/or couplers;
(e) about 1 to about 15 wt. % of two or more surfactants, preferably two or more surfactants, for example:
(e)(i) about 1 to 10 wt. % of one or more of nonionic surfactants; and
(e)(ii) optionally, about 0.1 to about 5 wt. % of one or more anionic surfactants;
(f) about 0.1 to about 5 wt. % of one or more thickening agents, preferably wherein at least one of the one or more thickening agents is a nonionic guar or modified guar gum such as hydroxypropyl guar;
(g) about 10 to about 50 wt. % of water;
(h) optionally, about 0.1 to about 5 wt. % of one or more reducing agents; and
(i) optionally, about 0.01 to about 10 wt. % of one or more miscellaneous ingredients;
wherein all percentages by weight are based on a total weight of the hair coloring base composition.

The hair coloring base composition may be in the form of an emulsion, for example, an oil-in-water emulsion or a water-in-oil emulsion.

In various embodiments, the hair coloring base composition improves smoothness, curl regularity, and/or curl definition of hair when used in a ready-to-use hair coloring composition to color the hair compared to a hair coloring base composition lacking coconut oil, but otherwise identical to the hair coloring base composition.

In various embodiments, the hair coloring base compositions are free or essentially free ammonia and ammonium-based compounds, e.g., ammonium hydroxide. An "ammonium-based compound" in the context of the instant disclosure is a compound which produces ammonia when in the composition at a particular pH. Examples of such compounds include ammonia and compounds which may be added as ammonium hydroxide and ammonium salts (e.g., simple salts). As ammonium salts, mention may be made of inorganic ammonium salts such as ammonium carbonate, ammonium bicarbonate, ammonium chloride, ammonium nitrate, ammonium sulfate, ammonium phosphate; organic ammonium salts such as ammonium formate, ammonium acetate, and tetramethylammonium hydroxide; and mixtures thereof.

In various embodiments, the hair coloring base composition is free or essentially free from polyorganosiloxanes (silicones).

In various embodiments, the hair coloring base composition is free or essentially free from amino silicones, for example, amodimethicone In various embodiments, the hair coloring base composition is free or essentially free from parabens.

In various embodiments, the hair coloring base compositions is free or essentially free from resorcinol.

In various embodiments, the hair coloring base composition is free or essentially free from film forming polymers.

In various embodiments, the hair coloring base composition is free or essentially free from fatty alcohols.

In various embodiments, the hair coloring base composition in the embodiment above improves smoothness, curl regularity, and/or curl definition of hair when used in a ready-to-use hair coloring composition to color the hair compared to a hair coloring base composition lacking coconut oil, but otherwise identical to the hair coloring base composition.

Coconut Oil

The total amount of coconut oil in the hair coloring base compositions will vary. Nonetheless, in various embodiments, the total amount of coconut oil in the hair coloring base compositions is from about 0.8 to about 2 wt. %, based on the total weight of the hair coloring base composition. In further embodiments, the total amount of coconut oils is from about 0.8 to about 1.9 wt. %, about 0.8 to about 1.8 wt. %, about 0.8 to about 2 wt. %, about 0.9 to about 1.9 wt. %, about 0.9 to about 1.8 wt. %, about 1 to about 2 wt. %, about 1 to about 1.9 wt. %, about 1 to about 1.8 wt. %, about 1.2 to about 2 wt. %, about 1.2 to about 1.9 wt. %, about 1.2 to about 1.8 wt. %, about 1.5 to about 2 wt. %, about 1.5 to about 1.9 wt. %, or about 1.5 to about 1.8 wt. %, based on the total weight of the hair coloring base composition.

Oil Other than Coconut Oil

The term "oil" means a "fatty substance" that is liquid, i.e. that is capable of flowing under the action of its own weight at room temperature (25° C.) and at atmospheric pressure ($10^5$ Pa). Preferably, the viscosity at a temperature of 25° C. and at a shear rate of 1 s$^{-1}$ of the oil is between $10^{-3}$ Pa·s and 2 Pa·s. It may be measured using a Thermo Haake RS600 rheometer with cone-plate geometry or an equivalent machine.

The term "fatty substance" means an organic compound that is insoluble in water at room temperature (25° C.) and at atmospheric pressure (760 mmHg) (solubility of less than 5%, preferably 1% and even more preferentially 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petrolatum or decamethylcyclopentasiloxane.

The one or more oils other than coconut oil do not contain any salified carboxylic acid groups. In addition, the one or more oils other than coconut oils are not (poly)oxyalkylenated or (poly)glycerolated ethers.

Among the oils, mention may be made of:
- halogenated or non-halogenated linear or branched hydrocarbons, of mineral or synthetic origin, containing less than 16 carbon atoms, for instance hexane, cyclohexane, undecane, dodecane, isododecane, tridecane or perfluorohexane, or more than 16 carbon atoms, such as liquid petroleum jelly;
- unsaturated or branched liquid fatty alcohols comprising from 6 to 30 carbon atoms, such as those of formula $C_nH_{2n+1}OH$ with n being an integer between 6 and 20 inclusive. Mention may be made especially of oleyl alcohol, linolenyl alcohol, linoleyl alcohol, ricinoleyl alcohol, undecylenyl alcohol, isostearyl alcohol and octyldodecanol.
- triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil; and
- liquid esters other than triglycerides.

These esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The oil may be a fluoro oil, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050° and PF 5060° by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052° by the company 3M.

The oil according to the invention may also be a liquid silicone oil. The term "liquid silicone" means an organopolysiloxane that is liquid at ordinary temperature (25° C.) and at atmospheric pressure (760 mmHg; i.e. $1.013 \times 10^5$ Pa).

Preferably, the silicone is chosen from liquid polydialkylsiloxanes, in particular liquid polydimethylsiloxanes (PDMSs), and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among the silicones containing aryl groups are polydiarylsiloxanes, in particular polydiphenylsiloxanes and polyalkylarylsiloxanes. The organomodified liquid silicones may especially contain polyethyleneoxy and/or polypropyleneoxy groups.

According to a preferred variant, the one or more oils other than coconut oil are chosen from $C_6$-$C_{16}$ lower alkanes; glycerides of plant or synthetic origin; linear or branched hydrocarbons of mineral or synthetic origin containing more than 16 carbon atoms; liquid fatty alcohols; liquid fatty esters; or mixtures thereof.

Even more preferentially, the one or more oils other than coconut oil are chosen from $C_6$-$C_{16}$ lower alkanes; linear or branched hydrocarbons of mineral or synthetic origin containing more than 16 carbon atoms; liquid fatty alcohols; or mixtures thereof.

Preferably, the one or more oils other than coconut oil are chosen from mineral oils such as liquid petroleum jelly, polydecenes, octyldodecanol and isostearyl alcohol, or mixtures thereof.

Preferably, the one or more oils other than coconut oil are chosen from isododecane and mineral oils, such as liquid petroleum jelly or mineral oil. More preferably the one or more oils other than coconut oil is mineral oil.

The total amount of the one or more oils other than coconut oil will vary. In various embodiments, the total amount of the one or more oils other than coconut oil is from about 50 to about 75 wt. %. If further embodiments, the total amount of the oil other than coconut oil is from about 50 to about 70 wt. %, about 50 to about 65 wt. %, about 55 to about 75 wt. %, about 55 to about 70 wt. %, or about 55 to about 65 wt. %, based on the total weight of the hair coloring base composition.

Alkalizing Agents

Alkalizing agents in the hair coloring base composition typically have multiple roles in the coloring process. For instance, the one or more alkalizing agents are helpful for obtaining a desired pH. In addition, the one or more alkalizing agents help cause the hair shaft to swell, allowing the small oxidative dye precursor molecules to penetrate the cuticle and cortex more easily. Also, the alkalizing agents can activate one or more oxidizing agents of the developer composition and contribute to the oxidation condensation process. Non-limiting examples of alkalizing agents include ammonia, ammonium hydroxide, ammonium carbonate, ammonium chloride, ammonium sulfate, ammonium nitrate, ammonium phosphate, ammonium acetate, ammonium hydrogen carbonate, ammonium carbamate, percarbonate salts, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates, and a mixture thereof.

The hair coloring base compositions according to the instant disclosure may include one or more alkalizing agents. According to various embodiments, the alkalizing agent may include at least one organic alkalizing agent and/or at least one mineral alkalizing agent.

In certain embodiments, the alkalizing agents are selected from organic alkalizing agents, for example, monoethanolamine, diethanolamine, triethanolamine, monoisopropanolamine, diisopropanolamine, triisopropanolamine, N,N-dimethylethanolamine, 2-amino-2-methyl-1-propanol, 2-amino-2-methyl-1,3-propanediol, 3-amino-1,2-propanediol, 3-dimethylamino-1,2-propanediol, tris(hydroxymethyl)amino-methane, or mixtures thereof. Monoethanolamine is particularly preferred.

In further embodiments, the alkalizing agents are selected from mineral alkalizing agents, for example, ammonia, ammonium carbonates, sodium carbonates, potassium carbonates, ammonium bicarbonates, sodium bicarbonates, potassium bicarbonates, ammonium hydroxides, sodium hydroxides, potassium hydroxides, or mixtures thereof. In some embodiments, the alkaline component comprises ammonia and/or ammonium hydroxide.

In some embodiments, the alkalizing agent comprises at least one organic alkalizing agent and is free or substantially free of mineral alkalizing agents. For example, the alkalizing agent may comprise less than about 0.5%, less than about less than about 0.3%, less than about 0.2%, less than about 0.1%, or less than about 0.05% of mineral alkalizing agents. In certain embodiments, the alkalizing agent comprises at least one organic alkalizing agent and is free or substantially free of ammonia and/or ammonium ions, and/or ammonium-based compounds. In various embodiments, the alkalizing agent comprises monoethanolamine. In further embodiments, the alkalizing agent comprises monoethanolamine and is free or substantially free of ammonia and/or ammonium ions and/or ammonium-based compounds. An "ammonium-based compound" in the context of the instant disclosure is a compound which produces ammonia when in the composition at a particular pH. Examples of such compounds include ammonia and compounds which may be added as ammonium hydroxide and ammonium salts (e.g., simple salts). As ammonium salts, mention may be made of inorganic ammonium salts such as ammonium carbonate, ammonium bicarbonate, ammonium chloride, ammonium nitrate, ammonium sulfate, ammonium phosphate; organic ammonium salts such as ammonium formate, ammonium acetate, and tetramethylammonium hydroxide; and mixtures thereof, The total amount of the one or more alkalizing agents in the hair coloring base compositions will vary. Nonetheless, in various embodiments, the total amount of the one or more alkalizing agents is from about 1 to about 10 wt. %, based on the total weight of the coloring base composition. In further embodiments, the total amount of the one or more alkalizing agents is from about 2 to about 10 wt. %, about 2 to about 8 wt. %, about 2 to about 6 wt. %, about 3 to about 10 wt. %, about 3 to about 8 wt. %, about 3 to about 6 wt. %, or about 4 to about 6 wt. %, based on the total weight of the hair coloring base composition.

Oxidative Dye Precursors and Couplers

Oxidative dye precursors are also referred to as "primary intermediates" or "oxidation bases." Oxidative dye precursors are often colorless or weakly colored compounds, which, when combined with oxidizing products, reactive via oxidative condensation to provide colored species. As oxidation dye precursors, use may be made of oxidation bases and couplers. By way of example, the oxidation bases are chosen from para-phenylenediamines, bis(phenyl)alkylenediamines, para-aminophenols, ortho-aminophenols and heterocyclic bases, and the addition salts thereof. Additional non-limiting examples include aromatic diamines, polyhydric phenols, amino phenols, and derivatives of these compounds, such as, for example, N-substituted derivatives of the amines, and ethers of the phenols, ortho- or para-aminophenols, ortho- or para-phenylenediamines, double bases, heterocyclic bases, and the acid addition salts thereof. More specific nonlimiting examples include dimethylpiperazinium aminopyrazolopyridine, 2,3-diaminodihydropyrazolo pyrazolone dimethosulfonate, p-phenylene diamine, 2,5-diaminotoluene, N,N-bis(2-hydroxymethyl)-p-phenylene diamine, paminophenol, salts thereof, etc.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-paraphenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Mention may be made, among bis(phenyl)alkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made, by way of example, of pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases of use in the present invention are the 3-aminopyrazolo[1,5-a]pyridine oxidation bases or addition salts thereof described, for example, in patent application FR2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Mention may be made, among pyrimidine derivatives such as 2,4,5,6-tetraamino-pyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2- dihydropyrazol-3-one or 2,3-diamino-6-hydroxy-6,7-dihydro-1H,5H-pyrazolo[1,2-a]pyrazol-1-one. Use is preferably made of 2,3-diamino-6,7-dihydro-1H,5H-pyrazolo[1,2-a]pyrazol-1-one and/or a salt thereof.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a salt thereof.

Among the couplers that may be used in the composition according to the invention, mention may be made in particular of meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles, quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and couplers are in particular chosen from the addition salts with an acid, such as the hydrochlorides, hydrobromides, sulfates, citrates, succinates, tartrates, lactates, tosylates, benzenesulfonates, phosphates and acetates.

The total amount of the one or more oxidative dye precursors and/or couplers will vary depending on the desired color and intensity of the hair to be treated. In various embodiments, the total amount of the one or more oxidative dye precursors and couplers is from about 0.001 to about 12 wt. %, about 0.001 to about 10 wt. %, about to about 8 wt. %, about 0.001 to about 5 wt. %, about 0.001 to about 4 wt. %, about to about 10 wt. %, about 0.01 to about 8 wt. %, about 0.01 to about 6 wt. %, or about to about 5 wt. %, about 0.01 to about 4 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.5 to about 12 wt. %, about 0.5 to about wt. %, about 0.5 to about 8 wt. %, about 0.5 to about 6 wt. %, about 0.5 to about 5 wt. %, or about 0.5 to about 4 wt. %, based on the total weight of the hair coloring base composition.

Surfactants

Surfactants can be nonionic, anionic cationic, amphoteric (zwitterionic) surfactants, or cationic. In various embodiments, the hair coloring base compositions include one or more nonionic surfactants. In further embodiments, the hair coloring base compositions include one or more nonionic surfactants and one of more anionic surfactants, for example, a fatty amide (nonionic surfactant) and an ether carboxylic acid (anionic surfactant).

Nonionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

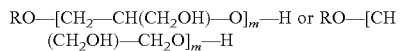

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

The nonionic surfactant may be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-40 hydrogenated castor oil.

Mixtures of these oxyethylenated derivatives of fatty alcohols and of fatty esters may also be used.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

In some cases, the nonionic surfactant is an oxyethylenated amide such as PEG-4 rapeseedamide.

Anionic Surfactants

Nonlimiting examples of anionic surfactants include alkyl sulfates, alkyl ether sulfates, alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, and a mixture thereof. Examples of alkyl sulfates and alkyl ether sulfates include sodium lauryl sulfate (SLS) or sodium dodecyl sulfate (SDS). In some instances, alky sulfates are particularly useful. Useful alkyl sulfates include $C_{8-18}$ alky sulfates, more preferably $C_{12-18}$ alkyl sulfates, preferably in the form of a salt with a solubilizing cation such as sodium, potassium, ammonium or substituted ammonium. Examples are sodium lauryl sulfate (SLS) or sodium dodecyl sulfate (SDS). Useful alkyl ether sulfates include those having the formula: $RO(CH_2CH_2O)_nSO_3M$; wherein R is an alkyl or alkenyl having from 8 to 18 (preferably 12 to 18) carbon atoms; n is a number having an average value of greater than at least preferably between 1 and 3, more preferably between 2 and 3; and M is a solubilizing cation such as sodium, potassium, ammonium or substituted ammonium. An example is sodium lauryl ether sulfate (SLES).

In certain embodiments, the hair coloring base composition includes one or more alkyl ether carboxylic acids. Nonlimiting examples of alkyl ether carboxylic acids include ceteareth-2 carboxylic acid, ceteareth-10 carboxylic acid, coceth-7 carboxylic acid, laureth-4 carboxylic acid, laureth-5 carboxylic acid, laureth-6 carboxylic acid, myreth-2 carboxylic acid, myreth-3 carboxylic acid, myreth-4 carboxylic acid, myreth-5 carboxylic acid, myreth-6 carboxylic acid, steareth-2 carboxylic acid, steareth-4 carboxylic acid, steareth-5 carboxylic acid, steareth-6 carboxylic acid, oleth-2 carboxylic acid, oleth-4 carboxylic acid, and mixtures and/or salts thereof.

The total amount of the one or more surfactants in the hair coloring base composition will vary. Nonetheless, in various embodiments, the total amount of the one or more surfactants is from about 0.5 to about 15 wt. %, based on the total weight of the hair coloring base composition. In further embodiments, the total amount of the one or more surfactants is from about 0.5 to about 12 wt. %, about 0.5 to about 10 wt. %, about 0.5 to about 8 wt. %, about 0.5 to about 6 wt. %, about 1 to about 15 wt. %, about 1 to about 12 wt. %, about 1 to about 10 wt. %, about 1 to about 8 wt. %, about 1 to about 6 wt. %, about 2 to about 15 wt. %, about 2 to about 12 wt. %, about 2 to about 10 wt. %, about 2 to about 8 wt. %, about 2 to about 6 wt. %, about 3 to about 15 wt. %, about 3 to about 12 wt. %, about 3 to about 10 wt. %, about 3 to about 8 wt. %, about 3 to about 6 wt. %, The total amount of the one or more nonionic surfactants, if present, will vary. Nonetheless, in various embodiments, the total amount of the one or more nonionic surfactants, if present, is from about 1 to about 10 wt. %, based on the total weight of the hair coloring base composition. In further embodiments, the total amount of the one or more nonionic surfactants is from about 1 to about 8 wt. %, about 1 to about 6 wt. %, about 1 to about 5 wt. %, about 2 to about 10 wt. %, about 2 to about 8 wt. %, about 2 to about 6 wt. %, about 2 to about 5 wt. %, about 3 to about 10 wt. %, about 3 to about 8 wt. %, about 3 to about 6 wt. %, or about 3 to about 5 wt. %, based on the total weight of the hair coloring base composition.

The total amount of the one or more anionic surfactants, if present, will vary. Nonetheless, in various embodiments, the total amount of the one or more anionic surfactants, if present, is from about 0.1 to about 5 wt. %, based on the total weight of the hair coloring base composition. In further embodiments, the total amount of the one or more anionic surfactants is from about 0.1 to about 5 wt. %, about 0.1 to about 4 wt. %, about 0.1 to about 3 wt. %, about 0.5 to about 5 wt. %, about 0.5 to about 4 wt. %, about 0.5 to about 3 wt. %, about 1 to about 5 wt. %, about 1 to about 4 wt. %, or about 1 to about 3 wt. %, based on the total weight of the hair coloring base composition.

Thickening Agents

Many thickening agents are known in the art. Nonlimiting examples include carboxylic acid polymers, crosslinked polyacrylate polymers, polyacrylamide polymers, polysaccharides, gums, modified gums, and a combination thereof. In particular, the following thickening agents are illustrative:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

c. Polyvinylpyrrolidone (PVP) and co-polymers: Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

d. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

e. Polyglyceryl esters: Non-limiting polyglycerol esters of fatty acids (polygylceryl esters) include those of the following formula:

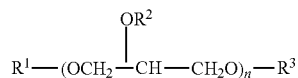

wherein n is from 2 to 20 or from 2 to 10 or from 2 to 5, or is 2, 3, 4, 5, 6, 7, 8, 9, or 10, and R1, R2 and R3 each may independently be a fatty acid moiety or hydrogen, provided that at least one of R1, R2, and R3 is a fatty acid moiety. For instance, R1, R2 and R3 may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

f. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-β-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-β-octadecenoic acid. More preferably, the aliphatic acid comprises 12-hydroxystearic acid, conjugated linoleic acid, or a mixture thereof.

g. Gums, including natural gums and modified gums: Non-limiting examples of gums include gum arabic, tragacanth gum, karaya gum, guar gum, gellan gum, tara gum, locust bean gum, tamarind gum, xanthan gum, locust bean gum, Seneca gum, *sclerotium* gum, gellan gum, derivatives thereof, etc.

In various embodiments, the hair coloring base compositions include one more guar gums including one or more derivatives of guar gums or modified guar gums, in particular, nonionic guar gums including one or more nonionic derivative of guar gums or nonionic modified guar gums. For simplicity, the term "nonionic guar gum" is intended to mean modified nonionic guar gums and unmodified nonionic guar gums.

Unmodified nonionic guar gums include, for example, the products sold under the name Vidogum GH 175 by the company Unipectine and under the names Meypro-Guar 50 and Jaguar C by the company Rhodia Chimie. Modified nonionic guar gums include, for example, guar gums modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups. Hydroxyalkylated guar gums are well known in the prior art and can be prepared, for example, by reacting corresponding alkene oxides such as, for example, propylene oxides, with the guar gum so as to obtain a guar gum modified with hydroxyalkyl groups and/or hydroxypropyl groups. The degree of hydroxyalkylation, which corresponds to the number of alkylene oxide molecules consumed by the number of free hydroxyl functions present on the guar gum, preferably ranges from 0.4 to 1.2. Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie or under the name GALACTASOL 4H4FD2 by the company Aqualon.

Also suitable are nonionic guar gums modified with hydroxyalkyl groups, more especially hydroxypropyl groups, modified with groups comprising at least one $C_6$-$C_{30}$ fatty chain. By way of example of such compounds, mention may be made, inter alia, of the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia Chimie.

The guar gums may optionally comprise at least one $C_6$-$C_{30}$ fatty chain.

The total amount of the one or more thickening agents will vary. Nonetheless, in various embodiments, the total amount of the one or more thickening agents is from about 0.1 to about 4 wt. %, about 0.1 to about 3 wt. %, about 0.1 to about 2 wt. %, about 0.5 to about 5 wt. %, about 0.5 to about 4 wt. %, about 0.5 to about 3 wt. %, about 0.5 to about 2 wt. %, or about 0.5 to about 1.5 wt. %, based on the total weight of the hair coloring base composition.

Water

The total amount of water in the hair coloring base composition will vary. Nonetheless, in various embodiments, the total amount of water is from about 10 to about 50 wt. %, based on the total weight of the hair coloring base compositions. In further embodiments, the total amount of water is from about 10 to about 40 wt. %, about 10 to about 40 wt. %, about 10 to about 35 wt. %, about 10 to about 30 wt. %, about 10 to about 25 wt. %, about 15 to about 50 wt. %, about 15 to about 40 wt. %, about 15 to about 35 wt. %, about 15 to about 30 wt. %, about 20 to about 50 wt. %, about 20 to about 40 wt. %, about 20 to about 35 wt. %, about 20 to about 30 wt. %, based on the total weight of the hair coloring base composition.

Reducing Agents

In various embodiments, the hair coloring base compositions include one or more reducing agents. Reducing agents are chemical species that lose an electron to another chemical species in a redox chemical reaction. Nonlimiting examples of reducing agents include ammonium bisulfite, ammonium sulfite, potassium metabisulfite, potassium sulfite, sodium hydrosulfite, sodium metabisulfite, sodium sulfite, sodium bisulphite, thioglycolic acid, thiolactic acid, thioglycerin, dehydroascorbic acid, a salt thereof, and a mixture thereof. In certain embodiments, the hair coloring base compositions include thioglycolic acid, thiolactic acid, thioglycerin, salts thereof, and mixtures thereof. In a preferred embodiment, the hair coloring base compositions include at least thioglycerin.

The total amount of the one or more reducing agents, if present, will vary. Nonetheless, in various embodiments, the total amount of the one or more reducing agents, if present, is from about 0.01 to about 5 wt. %, based on the total weight of the hair coloring base composition. In further embodiments, the total amount of the one or more reducing agents, if present, is from about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. %, based on the total weight of the hair coloring base composition.

Miscellaneous

The compositions the instant disclosure may optionally include (or optionally exclude) one more miscellaneous ingredients. Miscellaneous ingredients are ingredients that are compatible with the hair coloring compositions and do not disrupt or materially affect the basic and novel properties of the compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, cationic polymers, thickening agents, etc.

In various embodiments, the miscellaneous ingredients are chosen from preservatives, fragrances, pH adjusters, salts, chelating agents, buffers, composition colorants, and mixtures thereof.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

The total amount of the one or more miscellaneous ingredients, if present, will vary. Nonetheless, in various embodiments, the compositions of the instant disclosure include from about 0.001 to about 10 wt. % of one or more miscellaneous ingredients, based on the total weight of the composition. In further embodiments, the compositions of the instant disclosure include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the composition.

Water-Soluble Organic Solvents

In various embodiments, the hair coloring compositions of the instant disclosure (hair coloring base composition, developer compositions, or both) may include one or more water-soluble organic solvents (or simply "water-soluble solvents"). The term "water-soluble organic solvent" (or "water-soluble solvent") is interchangeable with the term "water-miscible solvent" and means an organic compound that is liquid at 25° C. and at atmospheric pressure (760 mmHg), and it has a solubility of at least 50% in water under these conditions. In certain embodiments, the one or more water-soluble organic solvents have a solubility of at least 60%, 70%, 80%, or 90% in water at 25° C. and at atmospheric pressure (760 mmHg). Non-limiting examples of water-soluble organic solvents include glycerin, alcohols (for example, $C_{1-30}$, $C_{1-15}$, $C_{1-10}$, or $C_{1-4}$ alcohols), polyols, glycols, and a mixture thereof. In certain embodiments, the one or more water-soluble organic solvents are chosen from alcohols such as ethyl alcohol, isopropyl alcohol, propyl alcohol, benzyl alcohol, and phenylethyl alcohol, or glycols or glycol ethers such as monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol.

Further non-limiting but useful examples of water-soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In various embodiments, the hair coloring compositions of the instant disclosure (hair coloring base composition, developer compositions, or both) includes one or more water-soluble organic solvents chosen from glycols, $C_{1-4}$ alcohols, glycerin, and a mixture thereof; preferably the water-soluble organic solvent is chosen from caprylyl glycol, glycerin, ethanol, isopropyl alcohol, dipropylene glycol, propylene glycol, hexylene glycol, caprylyl glycol, propylene glycol, glycerin, ethanol, and a mixture thereof.

In certain embodiments, the hair coloring compositions of the instant disclosure (hair coloring base composition, developer compositions, or both) includes one or more polyhydric alcohols. Nonlimiting examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble organic solvents will vary. In various embodiments, the hair coloring composition (hair coloring base composition, developer compositions, or both) includes about 0.1 to about 25 wt. % of the one or more water-soluble organic solvents, based on the total weight of the hair coloring composition. In further embodiments, the hair coloring composition (hair coloring base composition, developer compositions, or both) includes about 0.1 to about 20 wt. %, about 0.1 to about 15 wt. %, about 0.1 to about 10 wt. %, about 0.1 to about 5 wt. %, about 0.1 to about 3 wt. %, about 1 to about 25 wt. %, about 1 to about 20 wt. %, about 1 to about 15 wt. %, about 1 to about 10 wt. %, about 1 to about 5 wt. %, about 1 to about 3 wt. % of the one or more water-soluble organic solvents, based on the total weight of the coloring base composition (hair coloring base composition, developer compositions, or both).

Cationic Conditioning Polymers

In various embodiments, the hair coloring compositions of the instant disclosure (hair coloring base composition, developer compositions, or both) may include one or more cationic conditioning polymers. However, in other embodiments, the hair coloring compositions (hair coloring base composition, developer compositions, or both) are free or essentially free from cationic conditioning polymer.

Non-limiting examples of cationic polymers include copolymers of 1-vinyl-2-pyrrolidine and 1-vinyl-3-methylimidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). Additionally, or alternatively, the cationic conditioning polymers may include or be chosen from cationic guar gum derivatives, such as guar hydroxypropyltrimonium chloride.

In certain embodiments, the one or more cationic conditioning polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic).

Non-limiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Non-limiting examples of cationic guar include guar hydroxypropyltrimonium chloride, hydroxypropyl guar hydroxypropyltrimonium chloride, Non-limiting examples of cationic starch include starch hHydroxypropyltrimonium chloride, hydroxypropyl oxidized starch PG trimonium chloride, and a mixture thereof.

In various embodiments, the one or more cationic conditioning polymers are chosen from polyquaterniums. Non-limiting examples include Polyquaternium-1 (ethanol, 2,2', 2''-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In various embodiments, the one or more cationic conditioning polymers are chosen from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful. A particularly preferred and useful cationic polymer is polyquaternium-10.

The cationic polymers may be a polyquaternium. In certain embodiments, the cationic surfactants may be polyquaterniums selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

In some embodiments, the one or more cationic conditioning polymers are chosen from cationic proteins and cationic protein hydrolysates (e.g., hydroxypropyltrimonium hydrolyzed wheat protein), quaternary diammonium polymers (e.g., hexadimethrine chloride), copolymers of acrylamide and dimethyldiallyammonium chloride, and mixtures thereof.

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trademark) and LR (trademark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium- 24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride.

Polyquaterniums include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

If present the total amount of the one or more cationic conditioning polymers will vary. Nonetheless, in various embodiments, the total amount of the one or more cationic conditioning polymer is from about 0.01 to about 6 wt. %, based on the total weight of the hair coloring composition (hair coloring base composition, developer compositions, or both). In further embodiments, the total amount of the one or more cationic conditioning polymers is from about 0.01 to about 5 wt. %, about 0.01 to about 3 wt. %, about 0.05 to about 6 wt. %, about 0.05 to about 3 wt. %, about 0.1 to about 6 wt. %, about 0.1 to about 5 wt. %, about 0.1 to about 3 wt. %, based on the total weight of the hair coloring composition (hair coloring base composition, developer compositions, or both).

Viscosity

The viscosity of the hair coloring base composition is typically about 25 to about 150 cps at 25° C. using a #1 spindle at 100 rpm. By way of example only, the viscosity of the hair coloring base compositions may range from about 20 cps to about 150 cps, such as, for example, from about 20 to about 125 cps, about 20 to about 100 cps, about 20 to about 85 cps, about 20 to about 70 cps, about 25 to about 125 cps, about 25 to about 100 cps, about 25 to about 85 cps, about 25 to about 70 cps, about 30 to about 125 cps, about 30 to about 100 cps, about 30 to about 85 cps, about 30 to about 70 cps, about 50 to about 100 cps, about 60 to about 100 cps, about 70 to about 100 cps, about 50 to about 90 cps, about 50 to about 80 cps, or about 50 to about 75 cps, when measured at 25° C. using a M3 spindle at 100 rpm, for example, using a Rheomat RM 180.

In some non-limiting embodiments where the developer composition is liquid, e.g. aqueous, the developer composition may have a viscosity ranging from about 250 to about 2000 cps, such as, for example, from about 500 to about 2500 cps, about 500 to about 2000 cps, about 500 to about 1500 cps, about 600 to about 1300 cps, or about 650 to about 1200 cps when measured at 25° C. using a #4 spindle at 100 rpm, for example, using a Rheomat RM 180.

By way of example, the viscosity of the ready-to-use hair coloring composition can range from about 250 cps to about 2500 cps, such as, for example, from about 250 to about 2000 cps, about 250 to about 1800 cps, about 250 to about 1600 cps, about 300 to about 2000 cps, about 300 to about 1800 cps, about 300 to about 1600 cps, about 350 to about 2000 cps, about 350 to about 1800 cps, about 350 to about 1600 cps, about 400 to about 2000 cps, about 400 to about 1800 cps, about 400 to about 1600 cps, about 450 to about 2000 cps, about 450 to about 1800 cps, about 450 to about 1600 cps, about 500 to about 2000 cps, about 500 to about 1800 cps, or about 500 to about 1600 cps, when measured at 25° C. using a M3 spindle at 100 rpm, for example, using a Rheomat RM 180.

EMBODIMENTS

In various embodiments, the hair coloring base composition comprises or consists of:
(a) about 0.8 to about 2 wt. % of coconut oil;
(b) about 50 to about 75 wt. %, preferably from about 55 to 70 wt. %, more preferably about 55 to 65 wt. % of one or more oils other than coconut oil, preferably linear or branched hydrocarbons, of mineral or synthetic origin, containing less than 16 carbon atoms, for instance hexane, cyclohexane, undecane, dodecane, isododecane, tridecane or perfluorohexane, or more than 16 carbon atoms, such as liquid petroleum jelly or mineral oil, more preferably mineral oil, liquid petroleum jelly, polydecenes, octyldodecanol and isostearyl alcohol, or mixtures thereof, in particular, mineral oil;
(c) about 1 to about 15 wt. %, preferably about 2 to about 10 wt. %, more preferably about 3 to about 8 wt. % of one or more alkalizing agents, preferably one or more organic alkalizing agents, more preferably one or more organic alkalizing agents selected from alkanolamines, in particular monoethanolamine;
(d) one or more oxidative dye precursors and/or couplers, for example, from about 0.01 to about 8 wt. %, preferably from about 0.1 to about 6 wt. %, more preferably from about 1 to about 5 wt. %;
(e) about 1 to about 10 wt. % of one or more surfactants, preferably two or more surfactants, more preferably:
 (e)(i) about 1 to 8 wt. %, preferably about 1 to 6 wt. %, more preferably about 2 to about 5 wt. % of one or more of nonionic surfactants, preferably at least one alkoxylated nonionic surfactant, for example, a PEG-40 hydrogenated castor oil; and
 (e)(ii) about 0.1 to about 4 wt. %, preferably about 0.5 to about 3 wt. %, more preferably about 1 to about 2 wt. % of one or more anionic surfactants, for example, one or more anionic surfactants selected from alkyl sulfates, alkyl ether sulfates, alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, and a mixture thereof, preferably one or more sulfate surfactants, such as sodium lauryl sulfate;
(f) about 0.1 to about 5 wt. %, preferably about 0.1 to about 4, more preferably about 0.5 to about 3 wt. % of one or more thickening agents, for example, one or more thickening agents selected from carboxylic acid polymers, crosslinked polyacrylate polymers, polyacrylamide polymers, polysaccharides, gums, and a combination thereof, preferably selected from guar gums and modified guar gums, for example, hydroxypropyl guar gum;
(g) about 10 to about 50 wt. %, preferably from about 10 to about 40 wt. %, more preferably from about 15 to about 30 wt. % of water;
(h) optionally, about 0.01 to about 5 wt. %, preferably about 0.1 to about 3 wt. %, more preferably about 0.1 to about 2 wt. % of one or more reducing agents, for example, one or more reducing agents selected from potassium metabisulfite, potassium sulfite, sodium hydrosulfite, sodium metabisulfite, sodium sulfite, sodium bisulphite, thioglycolic acid, thiolactic acid, thioglycerin, dehydroascorbic acid, a salt thereof, and a mixture thereof, preferably thioglycerin.
(i) optionally, about 0.01 to about 10 wt. %, preferably about 0.1 to about 6 wt. %, more preferably about 1 to about 5 wt. % of one or more miscellaneous ingredients, for example, miscellaneous ingredients selected from preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, thickening agents, and mixtures thereof, preferably at least one or more preservatives, fragrances, pH adjusters, composition colorants, vitamins, chelating agents, and a combination thereof;

(j) optionally, about 0.01 to about 10 wt. %, preferably about 0.1 to about 6 wt. %, more preferably about 0.1 to about 5 wt. % of one or more water-soluble organic solvents, for example, one or more water-soluble organic solvents selected from glycerin, $C_1$-6 monoalcohols, polyols (polyhydric alcohols), glycols, and a mixture thereof, for example, monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol;

wherein all percentages by weight are based on a total weight of the hair coloring base composition.

In various embodiments, the hair coloring base composition in the embodiment above is in the form of an oil-in-water emulsion or a water-in-oil emulsion.

In various embodiments, the hair coloring base composition in the embodiment above has a viscosity of about 25 to about 150 cps at 25° C. using a #1 spindle at 100 rpm.

In various embodiments, the hair coloring base composition in the embodiment above does not visually phase separate or form visibly observable particulates for at least 8 weeks in storage at 25° C.

In various embodiments, the hair coloring base composition in the embodiment above is free or essentially free from polyorganosiloxanes (silicones).

In various embodiments, the hair coloring base composition in the embodiment above is free or essentially free from amino silicones, for example, amodimethicone In various embodiments, the hair coloring base composition in the embodiment above is free or essentially free from parabens.

In various embodiments, the hair coloring base compositions in the embodiment above is free or essentially free from resorcinol.

In various embodiments, the hair coloring base composition in the embodiment above is free or essentially free from film forming polymers.

In various embodiments, the hair coloring base composition in the embodiment above is free or essentially free from fatty alcohols.

In various embodiments, the hair coloring base composition in the embodiment above improves smoothness, curl regularity, and/or curl definition of hair when used in a ready-to-use hair coloring composition to color the hair compared to a hair coloring base composition lacking coconut oil, but otherwise identical to the hair coloring base composition.

Methods

The compositions of the instant disclosure are useful in methods for making ready-to-use hair coloring compositions and for methods of coloring hair. Methods for making a ready-to-use hair coloring composition include combining one or more hair coloring base compositions according to the instant disclosure with one or more developer compositions, including one or more developer compositions of the instant disclosure. However, the methods are not limited to developer compositions of the instant disclosure.

The one or more hair coloring base composition can be combined with the one or more developer compositions in a weight ratio of about 1:5 to about 5:1 (hair coloring base composition: developer composition). In some cases, the weight ratio is about 1:4 to about 4:1, about 1:3 to about 3:1, about 1:2 to about 2:1, or about 1:1 (hair coloring base composition: developer composition).

Methods for coloring hair, especially curly hair or very curly hair (Type 3 and Type 4), include applying a ready-to-use hair coloring composition of the instant disclosure to the hair. The ready-to-use hair coloring composition may be prepared as described above, i.e., by combining one or more hair coloring base compositions according to the instant disclosure with one or more developer compositions. The ready-to-use hair coloring composition is typically used (applied to hair) shortly after formation, i.e. shortly after the hair coloring base composition is combined with the developer composition to form a ready-to-use hair coloring composition, the ready-to-use hair coloring composition is applied to hair. In various embodiments, the ready-to-use hair coloring composition is applied to hair within about 1 hour after formation. In further embodiments, the ready-to-use hair coloring composition is applied to the immediately after formation up to about 1 hour after formation, up to about 45 minutes after formation, up to about 30 minutes after formation, or up to about 15 minutes after formation.

The ready-to-use hair coloring composition may be applied to hair of the head, hair of the body, facial hair (including beard hair and mustache hair), eyelashes, and/or eyebrows. In certain embodiments, the ready-to-use hair coloring composition is applied to curly hair or very curly hair (Type 3 and Type 4). In certain embodiments, the hair to be treated (colored) has been previously chemically treated, for example, previously bleached, previously colored, previously permed, previously straightened, etc. In further embodiments, the hair to be treated (colored) includes naturally grey hair, i.e., hair which has developed a loss of natural pigmentation and/or melanin.

After application to hair, the ready-to-use hair coloring composition remains on the hair for a period of time, for example, a period of sufficient to achieve a desired change in the color of the hair. For example, the ready-to-use hair coloring composition may be allowed to remain on the hair for up to 1 hour, such as from about 1 minute to about 60 minutes, about 1 minute to about 45 minutes, about 1 minute to about 30 minutes, about 1 minute to about 15 minutes, about 2 minutes to about 1 hour, about 2 minutes to about 45 minutes, about 2 minutes to about 30 minutes, about 2 minutes to about 15 minutes, about 2 minutes to about 10 minutes, about 3 minutes to about 30 minutes, about 3 minutes to about 25 minutes, about 3 minutes to about 20 minutes, about 3 minutes to about 15 minutes, about 3 minutes to about 10 minutes, or about 5 minutes to about 10 minutes. Those skilled in the art will, by considering various factors such as the starting and desired color of the hair, be able to determine an appropriate amount of time to leave the ready-to-use hair coloring composition on the hair to achieve the desired result. After the ready-to-use hair coloring composition has remained on the hair for a period of time, the ready-to-use hair coloring composition may be rinsed or cleansed (e.g., shampooed) from the hair.

In various embodiments, the hair coloring base composition in the embodiment above improves smoothness, curl regularity, and/or curl definition of hair when used in a ready-to-use hair coloring composition to color the hair compared to a hair coloring base composition lacking coconut oil, but otherwise identical to the hair coloring base composition. Accordingly, in various embodiments, the method improves smoothness, curl regularity, and/or curl definition of the hair compared to an identical method using a hair coloring base composition lacking coconut oil, but otherwise identical to the hair coloring base composition containing the coconut oil.

Forms

The hair coloring compositions of the instant disclosure (hair coloring base compositions, developer compositions, and ready-to-use hair coloring compositions) can be in a variety of forms. For example, in many instances, the compositions are in the form of a liquid, gel, lotion, crème, and/or spray. The compositions may be packaged in a variety of different containers. Nonlimiting examples of useful packaging include tubes, jars, caps, unit dose packages, bags, and bottles, including squeezable tubes and bottles.

Kits

The hair coloring base compositions of the instant disclosure may be present in a kit. For example, in certain embodiments, such kits include: (i) one or more hair coloring base compositions according to the instant disclosure; and (ii) one or more developer composition comprising one or more oxidizing agents; wherein the one or more hair coloring base compositions of (i) and the one or more developer compositions of (ii) are separately contained.

In some embodiments, the developer composition is aqueous or is in the form of an emulsion. The developer composition may include at least one solvent, for example, chosen from water, water-soluble organic solvents, and mixtures thereof.

In various exemplary embodiments, hydrogen peroxide is present in an amount of at least about 1% by weight, based on the total weight of the developer composition. In further embodiments, hydrogen peroxide is present in an amount ranging from about 0.1% to about 80% by weight, such as from about 1.0% to about 75% by weight, or from about 2% to about 10% by weight, based on the total weight of the developer composition. In further exemplary embodiments, the hydrogen peroxide may be present in the developer composition in an amount ranging from about 2% to about 25%, such as about 4% to about 20%, about 6% to about 15%, or about 7% to about 10%.

A cosmetically acceptable (water and/or a water-soluble organic solvent) carrier for the developer composition may, for example, be present in an amount ranging from about 0.5% to about 99% by weight, such as from about 5% to about 95% by weight, relative to the total weight of the developer composition.

In alternative embodiments, the developer composition is substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers, for example, to bound water, such as the water of crystallization of the salts or traces of water absorbed by the raw materials used in the preparation of the compositions according to embodiments of the disclosure.

When the developer composition is substantially anhydrous, the developer composition may comprise at least one solvent chosen from organic solvents. Suitable organic solvents for use in the developer composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The developer composition may be in the form of a powder, gel, liquid, foam, lotion, cream, mousse, and emulsion.

EXAMPLES

Implementation of the present disclosure is provided by way of the following examples. The examples serve to illustrate the technology without being limiting in nature.

Example 1

Compositions with Different % of Coconut Oil

|   |   |   | 1 | 2 | 3 | 4 | 5 | 6 |
|---|---|---|---|---|---|---|---|---|
| % Coconut Oil Testing | | | 0% | 0.1% | 1% | 1.8% | 3% | 5% |
| (a) | Coconut Oil | COCOS NUCIFERA OIL | | 0.1 | 1.0 | 1.8 | 3.0 | 5.0 |
| (b) | Additional Oil | MINERAL OIL | 60 | 60 | 60 | 60 | 60 | 60 |
| (c) | Alkalizing Agent | ETHANOLAMINE | 4.6 | 4.6 | 4.6 | 4.6 | 4.6 | 4.6 |
| (d) | Oxidative Dye and/or Couplers Precursors | HYDROXYETHYL-3,4-METHYLENEDIOXYANILINE HCL, HYDROXYBENZOMORPHOLINE, TOLUENE-2,5-DIAMINE, N,N-BIS(2-HYDROXYETHYL)-p-PHENYLENEDIAMINE SULFATE, m-AMINOPHENOL, AND 2,4-DIAMINOPHENOXY-ETHANOL HCL | ≤3 | ≤3 | ≤3 | ≤3 | ≤3 | ≤3 |

-continued

|     |                     |                                                      | 1    | 2    | 3    | 4    | 5    | 6    |
|-----|---------------------|------------------------------------------------------|------|------|------|------|------|------|
| (e) | Nonionic Surfactants | COCO-GLUCOSIDE AND/OR PEG-40 HYDROGENATED CASTOR OIL | 4.0  | 4.0  | 4.0  | 4.0  | 4.0  | 4.0  |
|     | Anionic Surfactant  | SODIUM LAURYL SULFATE                                | 1.2  | 1.2  | 1.2  | 1.2  | 1.2  | 1.2  |
| (f) | Thickening Agent    | HYDROXYPROPYL GUAR                                   | 1.0  | 1.0  | 1.0  | 1.0  | 1.0  | 1.0  |
| (h) | Reducing Agent      | SODIUM METABISULFITE AND/OR THIOGLYCERIN            | 0.2  | 0.2  | 0.2  | 0.2  | 0.2  | 0.2  |
| (i) | Miscellaneous Ingredients* |                                               | ≤5   | ≤5   | ≤5   | ≤5   | ≤5   | ≤5   |
| (g) | Water               |                                                      | QS   | QS   | QS   | QS   | QS   | QS   |
|     | pH                  |                                                      | 10.6 | 10.6 | 10.6 | 10.6 | 10.6 | 10.6 |
|     | Stable at 8 Weeks (25° C.) |                                               | Yes  | Yes  | Yes  | Yes  | Yes  | No   |
|     | Stable at 8 Weeks (45° C.) |                                               | Yes  | Yes  | Yes  | Yes  | No   | No   |

*buffering agents, preservatives, antioxidants, pH adjusters, salts, fragrances, chelating agents, vitamins, etc.

Example 2

| | | Compositions 1 wt. % Coconut Oil | | | | | | | | | |
|---|---|---|---|---|---|---|---|---|---|---|---|
| | | Inventive | | | | | | Comparative | | | |
| | Ingredients | A | B | C | D | E | F | C1 | C2 | C3 | C4 |
| | | Amounts (wt. %) | | | | | | | | | |
| (a) Coconut Oil | COCOS NUCIFERA OIL | 1.0 | 1.0 | 1.0 | 1.0 | 1.0 | 1.0 | | | | |
| (b) Additional Oil | MINERAL OIL | 60 | 60 | 60 | 60 | 60 | 60 | 60 | 60 | 60 | 60 |
| (c) Alkalizing Agent | ETHANOLAMINE | 4.6 | 4.5 | 4.5 | 4.6 | 4.4 | 4.4 | 4.5 | 4.4 | 4.4 | 4.4 |
| (d) Oxidative Dye Precursors and/or Couplers* | HYDROXYETHYL-3,4-METHYLENEDIOXYANILINE HCL, 2-AMINO-3-HYDROXYPYRIDINE, HYDROXYBENZO-MORPHOLINE, TOLUENE-2,5-DIAMINE, N,N-BIS(2-HYDROXYETHYL)-p-PHENYLENEDIAMINE SULFATE, m-AMINOPHENOL, AND/OR 2,4-DIAMINOPHENOXY-ETHANOL HCL | ≤3 | ≤3 | ≤3 | ≤3 | ≤3 | ≤3 | ≤3 | ≤3 | ≤3 | ≤3 |
| (e) Nonionic Surfactants | COCO-GLUCOSIDE AND/OR PEG-40 HYDROGENATED CASTOR OIL | 4.0 | 4.0 | 4.0 | 4.0 | 4.0 | 4.0 | 4.0 | 4.0 | 4.0 | 4.0 |
| Anionic Surfactant | SODIUM LAURYL SULFATE | 1.2 | 1.2 | 1.2 | 1.2 | 1.2 | 1.2 | 1.2 | 1.2 | 1.2 | 1.2 |
| (f) Thickening Agent | HYDROXYPROPYL GUAR | 1.0 | 1.0 | 1.0 | 1.0 | 1.0 | 1.0 | 1.0 | 1.0 | 1.0 | 1.0 |
| (h) Reducing Agent | SODIUM METABISULFITE, AND/OR THIOGLYCERIN | 0.2 | 0.2 | 0.2 | 0.2 | 0.2 | 0.2 | 0.2 | 0.2 | 0.2 | 0.2 |
| (i) | Miscellaneous Ingredients** | ≤5 | ≤5 | ≤5 | ≤5 | ≤5 | ≤5 | ≤5 | ≤5 | ≤5 | ≤5 |
| (g) | Water | qs | qs | qs | qs | qs | qs | qs | qs | qs | qs |
| | pH | 10.6 | 10.6 | 10.6 | 10.6 | 10.6 | 10.6 | 10.9 | 10.9 | 10.9 | 10.9 |

*The compositions differ with respect to the (d) oxidative dye precursors and/or couplers, i.e., the compositions impart different colors to the hair.

**buffering agents, preservatives, antioxidants, pH adjusters, salts, fragrances, chelating agents, vitamins, etc.

Example 3

| | | Compositions 1.8 wt. % Coconut Oil | | | | |
|---|---|---|---|---|---|---|
| | | Inventive | | | | Comp. |
| | | G | H | I | J | C-5 |
| | Ingredients | Amounts (wt. %) | | | | |
| (a) Coconut Oil | COCOS NUCIFERA OIL | 1.8 | 1.8 | 1.8 | 1.8 | |
| (b) Additional Oil | MINERAL OIL | 60 | 60 | 60 | 60 | 60 |
| (c) Alkalizing Agent | ETHANOLAMINE | 4.6 | 4.5 | 4.5 | 4.5 | 4.5 |
| (d) Oxidative Dye Precursors and/or Couplers | 2-AMINO-3-HYDROXYPYRIDINE, HYDROXYBENZOMORPHOLINE, N,N-BIS(2-HYDROXYETHYL)-p-PHENYLENEDIAMINE SULFATE, m-AMINOPHENOL, 2,4-DIAMINOPHENOXYETHANOL HCL, HYDROXYETHYL-3,4-METHYLENEDIOXYANILINE HCL, AND/OR TOLUENE-2,5-DIAMINE | | | | | |
| (e) Nonionic Surfactants | COCO-GLUCOSIDE, AND/OR PEG-40 HYDROGENATED CASTOR OIL | 4.0 | 4.0 | 4.0 | 4.0 | 4.0 |
| Anionic Surfactant | SODIUM LAURYL SULFATE | 1.2 | 1.2 | 1.2 | 1.2 | 1.2 |
| (f) Thickening Agent | HYDROXYPROPYL GUAR | 1.0 | 1.0 | 1.0 | 1.0 | 1.0 |
| (h) Reducing Agents | SODIUM METABISULFITE, AND/OR THIOGLYCERIN | 0.2 | 0.2 | 0.2 | 0.2 | 0.2 |
| (i) | Miscellaneous** | ≤5 | ≤5 | ≤5 | ≤5 | ≤5 |
| (g) Water | WATER | 23.6 | 24.5 | 25.7 | 25.2 | 26.3 |
| pH | | 10.6 | 10.6 | 10.6 | 10.6 | 10.9 |

* The compositions differ with respect to the (d) oxidative dye precursors and/or couplers, i.e., the compositions impart different colors to the hair.
**buffering agents, preservatives, antioxidants, pH adjusters, salts, fragrances, chelating agents, vitamins, etc.

| | | | (wt. %) | |
|---|---|---|---|---|
| | | | X | Y |
| | Developer Compositions | | 20 V | 30 V |
| (a) | Oxidizing Agent | HYDROGEN PEROXIDE | 6.0 | 6.0 |
| (b) | Water-Soluble Solvent | GLYCERIN | 0.5 | 0.5 |
| (c) | Oil | MINERAL OIL | 2.0 | 25.0 |
| (d) | Fatty Alcohol | CETEARYL ALCOHOL | 6.0 | 6.0 |
| (e) | Nonionic Surfactants | PEG-4 RAPESEEDAMIDE AND/OR STEARETH-20 | 6.2 | 6.2 |
| (f) | Cationic Conditioning Polymer | POLYQUATERNIUM-6 | 0.2 | 0.2 |
| (h) | Miscellaneous (buffering agents, preservatives, antioxidants, pH adjusters, salts, fragrances, chelating agents, vitamins, etc. | TETRASODIUM PYROPHOSPHATE, HEXADIMETHRINE CHLORIDE, TOCOPHEROL, SODIUM SALICYLATE, TETRASODIUM ETIDRONATE, AND TETRASODIUM EDTA | ≤3 | ≤3 |
| (g) | | WATER | qs | qs |

Example 4

Developer

Example 5

Stability Testing

The stability of the compositions of Example 1 was assessed. The compositions were stored at 4° C., 25° C., and 45° C. for 4 weeks and visually inspected for signs of phase separation. The compositions were also stored at 25° C. and 45° C. for 8 weeks and visually inspected for signs of phase separation. The results are shown in the Table of Example 1.

Example 6

Cosmetic Testing

A hair color study was carried to determine and assess the cosmetic benefits provided by coconut oil in hair color compositions. Six female volunteers having curly and greying hair participated in the study. The Inventive Composition H from Example 4 was compared with Comparative Composition C-5 from Example 4. The compositions are identical except that Inventive Composition H includes 1.8 wt. % of coconut oil.

Inventive Composition H and Comparative Composition C-5 were separately mixed in a 1:1 weight ratio with Developer Composition X from Example 5 to form ready-to-use hair coloring compositions. The inventive ready-touse hair coloring composition was applied to half of each volunteers' head of hair (applied near the scalp around the roots of the hair); and the comparative ready-to-use hair coloring composition was applied to the other half of each volunteers' head of hair (applied near the scalp around the roots of the hair). The ready-to-use hair coloring compositions were allowed to remain on the hair (for processing) for 25 minutes, then pulled through the entirety of the hair, and allowed to remain on the entirety of the hair (for processing) for 10 additional minutes (for a total processing time of 35 minutes). After 35 minutes, both of the ready-to-use hair coloring compositions were rinsed from the hair. The hair was washed with a standard shampoo and conditioned with a standard rinse-out conditioner. After shampooing and conditioning the colored hair, the hair was evaluated in the wet/damp state and again after air drying at ambient temperature (~25° C.).

A panel of 9 different expert evaluators assess the colored hair for a variety of cosmetic attributes. The evaluators assessed the hair while damp/wet and after it dried. Each evaluated scored the attribute on a scale from 1 to 3 (1 being minimal or no effect and 3 being the excellent or best effect). The scores were averaged for each attribute and summarized as follows:

| Scoring System | Difference | Designation |
| --- | --- | --- |
| Average Score Differs by Less than 1 | Not Different | |
| Average Score Differs by 1 to Less than 2 | Noticeably Better | + |
| Average Score Differs by 2 or More | Significantly Better | ++ |

The differences between Attributes that differed are shown in the tables below.

| Pre-Shampooing Observations | Inventive H | Comparative C-5 |
| --- | --- | --- |
| Ease of Detangling | + | |
| Degree of Coating | ++ | |

| Wet Hair (Post Shampoo/Conditioner) | Inventive H | Comparative C-5 |
| --- | --- | --- |
| Smoothness | ++ | |
| Volume | | + |
| Degree of Coating | ++ | |

| Wet Hair (Curl Observation) | Inventive H | Comparative C-5 |
| --- | --- | --- |
| Curl Regularity | + | |
| Curl Definition | + | |

| Dry Hair | Inventive H | Comparative C-5 |
| --- | --- | --- |
| Discipline | + | |
| Shine | | + |
| Degree of Coating | + | |

| Dry Hair (Curl Observation) | Inventive H | Comparative C-5 |
| --- | --- | --- |
| Discipline | + | |
| Shine | | + |
| Degree of Coating | + | |

As shown by the tables above, the hair colored with Inventive Composition H was ranked better than hair colored with Comparative Composition C-5 for most attributes. Also, hair colored with Inventive Composition H showed significantly better (++) coating before the hair was shampooed and conditioned; and showed significantly better (++) smoothness and coating after being shampooed and conditioned. Finally, the hair treated with Inventive Composition H showed better overall characteristics that are particularly important for curly hair, e.g., curl definition, curl regularity, and discipline.

Example 7

Different Natural Oils and Fats

Commercial benchmark products having various types of oils and fats were identified. The commercial benchmark products did not include coconut oil. Instead, they included olive oil, shea butter, or jojoba oil, respectively. The commercial benchmark products and the composition containing coconut oil were used to treat hair swatches (Type 3 curly or Type 4 coily). Expert evaluators examined the treated hair swatches for overall conditioning, smoothness, curl definition, and curl regularity. The experts found that compositions containing coconut oil provide a greater degree of conditioning (smoothness, curl definition, and curl regularity) than the commercial benchmark products containing olive oil, shea butter, and jojoba oil. The experts concluded that coconut oil is unique and different from the other oils by providing better conditioning properties to the hair. Without being bound by any particular theory, the inventors believe that coconut oil has a particularly high affinity for the hair. It is readily deposited onto the hair and penetrates into the hair fiber.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

The term "hair" as used herein includes hair of the head, the face (including beard hair and mustache hair), eyebrows, eyelashes, and body hair, unless otherwise specified.

As used herein, the terms "comprising," "having," and "including" are used in their open, non-limiting sense.

A "developer composition" as used herein is a composition containing one or more oxidizing agents, preferably a peroxide (hydrogen peroxide) and is mixed with a hair coloring base composition to form a ready-to-use hair coloring composition.

A "hair coloring base composition" as used herein is a hair coloring composition containing one or more oxidative dye precursors and is mixed with a developer composition to form a ready-to-use hair coloring composition.

A "ready-to-use hair coloring composition" is an "active" composition that includes one or more oxidative dye precursors and one or more oxidizing agents; and is formed by combining a hair coloring base composition with a developer composition.

A "composition colorant" is a compound that colors the composition but does not have an appreciable coloring effect on hair. In other words, the composition colorant is included to provide color to the composition, for example, for aesthetic appeal. It is not included to impart color to the hair. Styling gels, for example, can be found in a variety of different colors (e.g., light blue, light pink, etc.) yet application of the styling gel to the hair does not change the color of the hair.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a nonionic surfactant may be considered both a nonionic surfactant and a fatty compound or oil. If a particular composition includes both a nonionic surfactant and a fatty compound or oil, a single compound will serve as only the nonionic surfactant or the fatty compound/oil (the single compound does not serve as both the nonionic surfactant and the fatty component/oil).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto a keratinous substrate such as hair. The term 'treat" (and its grammatical variations) as used herein also refers to contacting keratinous substrates such as hair with the compositions of the present disclosure.

As used herein, all ranges provided are meant to include every specific range within, and combination of sub ranges between, the given ranges. Thus, a range from 1-includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

All components positively set forth throughout the instant disclosure may be negatively excluded from the claims, e.g., a claimed composition may be "free," "essentially free" (or "substantially free") of one or more components that are positively set forth in the instant disclosure. As an example, silicones can optionally be included in the compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes.

The term "substantially free" or "essentially free" as used herein means that there is less than about 3% by weight of a specific material added to a composition, based on the total weight of the compositions. Nonetheless, the compositions may include less than 2 wt. %, less than about 1 wt. %, less than about 0.5 wt. %, less than about 0.1 wt. %, or none of the specified material.

All components set forth herein may be optionally included or excluded from the compositions/method/kits. When excluded, the compositions/methods/kits may be free or essentially free of the component.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring base composition comprising:
   (a) about 0.8 to about 2 wt. % of coconut oil;
   (b) about 50 to about 75 wt. % of one or more oils other than coconut oil chosen from ester oils, silicone oils, fluoro oils, vegetable oils, animal oils, hydrocarbon-based oils, or combinations thereof;
   (c) about 1 to about 15 wt. % of one or more alkanolamines;
   (d) one or more oxidative dye precursors and/or couplers;
   (e) about 1 to about 10 wt. % of one two or more surfactants, wherein the two or more surfactants include:
      (e)(i) about 1 to 8 wt. % of one or more of nonionic surfactants; and
      (e)(ii) about 0.1 to about 4 wt. % of one or more anionic surfactants;
   (f) about 0.1 to about 5 wt. % of one or more thickening agents; and
   (g) about 10 to about 50 wt. % of water;
      wherein all percentages by weight are based on a total weight of the hair coloring base composition.

2. The hair coloring base composition of claim 1, wherein the one or more oxidative dye precursors and/or couplers of (d) are selected from para-phenylenediamines, bis(phenyl) alkylenediamines, para-aminophenols, ortho-aminophenols, toluene-2,5-diamine and heterocyclic bases, the addition salts thereof, or combinations thereof.

3. The hair coloring composition of claim 1, wherein the one or more thickening agents of (f) are selected from carboxylic acid polymers, crosslinked polyacrylate polymers, polyacrylamide polymers, polysaccharides, gums, or combinations thereof.

4. The hair coloring composition of claim 3, wherein the one or more thickening agents of (f) are selected from nonionic guar gums, modified guar gums, or combinations thereof.

5. The hair coloring composition of claim 4, wherein the one or more thickening agent of (f) is selected from hydroxyalkylated guar gums.

6. The hair coloring composition of claim 1, wherein the water of (g) is in an amount of from about 10 wt. % to about 40 wt. %.

7. The hair coloring base composition of claim 1, wherein the one or more oxidative dye precursors and/or couplers are in an amount from about 0.01 to about 5 wt. %.

8. The hair coloring base composition of claim 1, further comprising one or more reducing agents.

9. The hair coloring base composition of claim 8, wherein the one or more reducing agents are chosen from potassium metabisulfite, potassium sulfite, sodium hydrosulfite, sodium metabisulfite, sodium sulfite, sodium bisulphite, thioglycolic acid, thiolactic acid, thioglycerin, dehydroascorbic acid, a salt thereof, and a mixture thereof.

10. The hair coloring base composition of claim 1, further comprising one or more miscellaneous ingredients selected from preservatives, fragrances, pH further adjusters, salts, chelating agents, buffers, antioxidants, flavonoids, vitamins, botanical extracts, UV filtering agents, proteins, protein hydrolysates, protein isolates, fillers, composition colorants, cationic polymers, thickening agents, or mixtures thereof.

11. A kit comprising:
   (i) one or more hair coloring base compositions of claim 1; and
   (ii) one or more developer compositions comprising:
      (a) one or more oxidizing agents; and
      (b) water;
      wherein the one or more hair coloring base compositions of (i) and the one or more developer compositions of (ii) are separately contained.

12. A ready-to-use hair coloring composition comprising a mixture of:
   (i) the hair coloring base composition of claim 1; and
   (ii) a developer composition comprising:
      (a) one or more oxidizing agents; and
      (b) water;
      wherein the hair coloring base composition of (i) and the developer composition of (ii) are mixed in a ratio of about 5:1 to 1:5.

13. The ready-to-use hair coloring composition of claim 12, whereby at least one of curl definition, curl regularity, and discipline is improved upon being applied to curly or very curly hair as compared to using a ready-to-use hair coloring composition that does not contained the claimed amounts of coconut oil.

14. The hair coloring base composition of claim 1, which comprises (b) about 55 to about 75 wt. % of one or more oils other than coconut oil; (g) about 10 to about 40 wt. % of water; wherein the composition has a pH of about 9 or higher, and has a viscosity of about 25 to about 150 cps at 25° C. using a #1 spindle at 100 rpm.

15. The hair coloring base composition of claim 14, which comprises (a) about 1.2 to about 2 wt. % of coconut oil.

16. The hair coloring base composition of claim 1, which comprises (a) about 1.2 to about 2 wt. % of coconut oil.

17. The hair coloring base composition of claim 1, further comprising one or more reducing agents selected from the group consisting of thioglycolic acid, thiolactic acid, thioglycerin, salts thereof, and mixtures thereof.

18. The hair coloring base composition of claim 1, further comprising one or more reducing agents selected from the group consisting of thioglycerin and salts thereof.

19. The hair coloring base composition of claim 1, wherein the one or more oils other than coconut oil comprise at least one member selected from the group consisting of hexane, cyclohexane, undecane, dodecane, isododecane, tridecane, perfluorohexane, mineral oil and liquid petroleum jelly.

20. The hair coloring base composition of claim 1, which comprises (a) about 0.9 to about 1.8 wt. % of coconut oil.

21. A hair coloring base composition comprising:
   (a) about 0.8 to about 2 wt. % of coconut oil;
   (b) about 50 to about 75 wt. % of mineral oil;
   (c) about 1 to about 10 wt. % of one or more alkanolamines;
   (d) one or more oxidative dye precursors and/or couplers;
   (e) about 1 to about 15 wt. % of two or more surfactants, wherein the two or more surfactants include:
      (e)(i) about 1 to 10 wt. % of one or more of nonionic surfactants; and
      (e)(ii) about 0.1 to about 5 wt. % of one or more anionic surfactants;
   (f) about 0.1 to about 5 wt. % of one or more thickening agents selected from nonionic guar gum, modified guar gum, or combinations thereof,
   (g) about 10 to about 50 wt. % of water; and
   (h) one or more reducing agents;
   wherein the composition has a pH of about 9 or higher, and
   all percentages by weight are based on a total weight of the hair coloring base composition.

22. A method for coloring curly or very curly hair comprising:
   (i) obtaining the hair coloring base composition of claim 21;
   (ii) obtaining a developer composition comprising:
      (a) one or more oxidizing agents; and
      (b) water;
   (iii) mixing the hair coloring base composition of (i) and the developer composition of (ii) in a weight ratio of about 1:5 to about 5:1 to form a ready-to-use hair coloring composition; and
   (iv) applying the ready-to-use hair coloring composition to hair;
   (v) allowing the ready-to-use hair coloring composition to remain on the hair for a period of time of about 1 minute to about 60 minutes; and
   (vi) after the period of time, rinsing the ready-to-use hair coloring composition from the hair;
   thereby improving at least one of curl definition, curl regularity, and discipline as compared to using a ready-to-use hair coloring composition that does not contained the claimed amounts of coconut oil.

23. The hair coloring base composition of claim 21, wherein the (c) one or more alkanolamines comprises ethanolamine.

24. The hair coloring base composition of claim 21, wherein the one or more oxidative dye precursors and/or couplers of (d) are selected from para-phenylenediamines, bis(phenyl)alkylenediamines, para-aminophenols, ortho-aminophenols, toluene-2,5-diamine and heterocyclic bases, the addition salts thereof, or combinations thereof.

25. The hair coloring base composition of claim 21, wherein the (e)(i) one or more of nonionic surfactants are selected from the group of decylglucoside, caprylyl/capryl glucoside, laurylglucoside, coco-glucoside, cetostearyl glucoside, arachidyl glucoside, cocoylethylglucoside, PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-40 hydrogenated castor oil, and combinations thereof, and the (e)(ii) one or more anionic surfactants are selected from the group of sodium dodecyl sulfate and sodium lauryl sulfate and combinations thereof.

26. The hair coloring base composition of claim 21, wherein the (e)(i) one or more of nonionic surfactants are selected from the group of coco-glucoside and PEG-40 hydrogenated castor oil, and combinations thereof; and the (e)(ii) one or more anionic surfactants comprises sodium lauryl sulfate.

27. The hair coloring base composition of claim 21, wherein the (c) one or more alkanolamines comprises ethanolamine; the one or more oxidative dye precursors and/or couplers of (d) are selected from para-phenylenediamines, bis(phenyl)alkylenediamines, para-aminophenols, ortho-aminophenols, toluene-2,5-diamine and heterocyclic bases, the addition salts thereof, or combinations thereof, and the (e)(i) one or more of nonionic surfactants are selected from the group of coco-glucoside and PEG-40 hydrogenated castor oil, and combinations thereof; and the (e)(ii) one or more anionic surfactants comprises sodium lauryl sulfate.

28. The hair coloring base composition of claim 21, which has a viscosity of about 25 to about 150 cps at 25° C. using a #1 spindle at 100 rpm.

\* \* \* \* \*